US012644155B2

(12) United States Patent
Zhao et al.

(10) Patent No.: US 12,644,155 B2
(45) Date of Patent: Jun. 2, 2026

(54) MOLECULAR PROBE FOR NUCLEIC ACID DETECTION, PREPARATION AND USE THEREOF

(71) Applicant: GE Healthcare AS, Oslo (NO)

(72) Inventors: Zhoushe Zhao, Beijing (CN); Hongli Li, Beijing (CN); Yanmei Wang, Beijing (CN)

(73) Assignee: GE Healthcare AS, Oslo (NO)

( * ) Notice: Subject to any disclaimer, the term of this patent is extended or adjusted under 35 U.S.C. 154(b) by 481 days.

(21) Appl. No.: 18/016,444

(22) PCT Filed: Jul. 16, 2021

(86) PCT No.: PCT/EP2021/070059
§ 371 (c)(1),
(2) Date: Jan. 16, 2023

(87) PCT Pub. No.: WO2022/013451
PCT Pub. Date: Jan. 20, 2022

(65) Prior Publication Data
US 2024/0167091 A1     May 23, 2024

(30) Foreign Application Priority Data

Jul. 17, 2020    (CN) .......................... 202010691487.8

(51) Int. Cl.
*C12Q 1/6816*          (2018.01)
*C12Q 1/6883*          (2018.01)
(52) U.S. Cl.
CPC ......... *C12Q 1/6883* (2013.01); *C12Q 1/6816* (2013.01); *C12Q 2600/158* (2013.01)
(58) Field of Classification Search
CPC .. C12Q 1/6883; C12Q 1/6816; C12Q 1/6813; C12Q 1/6841; C12Q 2600/158;
(Continued)

(56) References Cited

U.S. PATENT DOCUMENTS

2004/0063628 A1* 4/2004 Piccariello ............. A61K 47/62
514/21.8
2005/0130167 A1 6/2005 Bao et al.
(Continued)

FOREIGN PATENT DOCUMENTS

CN        103201386 A     7/2013
JP        2012525146 A    10/2012
(Continued)

OTHER PUBLICATIONS

Martin et al., "Intracellular Fate of Peptide-Mediated Delivered Cargoes," Current Pharmaceutical Designs, 2013, 19, 20 pages.
(Continued)

*Primary Examiner* — Samuel C Woolwine
*Assistant Examiner* — Francesca Filippa Giammona
(74) *Attorney, Agent, or Firm* — Lathrop GPM LLP; Malaika O.D. Tyson

(57)          ABSTRACT

The present disclosure relates to molecular probes for nucleic acid detection, and preparation and uses thereof. In particular, described herein is a molecular probe for detection of a nucleic acid, comprising, (1) a molecular probe carrier which comprises a cell penetrating peptide and a detectable label coupled to the cell penetrating peptide, and (2) a targeting oligonucleotide, wherein the targeting oligonucleotide is attached to the molecular probe carrier. Also described herein are a method for preparing the molecular probe, a method for detection of a nucleic acid, and a kit for detection of a nucleic acid.

8 Claims, 5 Drawing Sheets

Specification includes a Sequence Listing.

FIG. 1

(58) Field of Classification Search
CPC ........... A61K 49/0438; A61K 49/0002; A61K
49/0021; A61K 51/0491
See application file for complete search history.

(56) References Cited

U.S. PATENT DOCUMENTS

| 2006/0068433 | A1* | 3/2006 | Godfrey | ............... | C12Q 1/6851 |
| | | | | | 435/6.1 |
| 2009/0156470 | A1 | 6/2009 | Chatterton | | |
| 2015/0297742 | A1 | 10/2015 | Strieker et al. | | |

FOREIGN PATENT DOCUMENTS

| WO | | 03106491 | A2 | 12/2003 | | |
| WO | | 2004083902 | A2 | 9/2004 | | |
| WO | | 2007069068 | A2 | 6/2007 | | |
| WO | WO-2012064429 | A2 * | 5/2012 | | .............. | A61P 37/02 |
| WO | | 2016177899 | A1 | 11/2016 | | |
| WO | | 2020010103 | A1 | 1/2020 | | |
| WO | WO-2021134023 | A2 * | 7/2021 | | ......... | A61K 47/6929 |

OTHER PUBLICATIONS

Search Report received in International Application No. PCT/EP2021/070059 dated Oct. 29, 2021, 6 pages.

Written Opinion received in International Application No. PCT/EP2021/070059 dated Oct. 29, 2021, 7 pages.

Tai et al., "Functional peptides for siRNA delivery," Advanced Drug Delivery Reviews, 2017, Aug. 13, 2016, 12 pages.

China National IP Administration, "First Office Action regarding Application No. 202010691487.8," 14 pages, including English translation, dated Oct. 27, 2023.

Japanese Patent Office, Office Action for JP Patent Application No. 2023-502884, dated Jul. 29, 2025.

Mandal et al., "Cell-penetrating homochiral cyclic peptides as nuclear-targeting molecular transporters", Angew Chem. Int. Ed. Engl., Oct. 4, 2011, 50(41): 9633-9637. Epub Sep. 15, 2011.

Shirazi et al., "Cyclic peptide-capped gold nanoparticles as drug delivery systems", Mol. Pharm., Feb. 4, 2013, 10(2): 500-511. Epub Oct. 5, 2012.

* cited by examiner

FIG. 1

SEQUENCE LISTING

```
<160> NUMBER OF SEQ ID NOS: 7

<210> SEQ ID NO 1
<211> LENGTH: 10
<212> TYPE: PRT
<213> ORGANISM: Artificial Sequence
<220> FEATURE:
<223> OTHER INFORMATION: The sequence is artificially synthesized
<220> FEATURE:
<221> NAME/KEY: MISC_FEATURE
<222> LOCATION: (1)..(10)
<223> OTHER INFORMATION: Peptide is circular

<400> SEQUENCE: 1

Trp Arg Trp Arg Trp Lys Trp Arg Trp Arg
1               5                   10

<210> SEQ ID NO 2
<211> LENGTH: 21
<212> TYPE: RNA
<213> ORGANISM: Artificial Sequence
<220> FEATURE:
<223> OTHER INFORMATION: The sequence is artificially synthesized
<220> FEATURE:
<221> NAME/KEY: modified_base
<222> LOCATION: (1)..(1)
<223> OTHER INFORMATION: 2-Prime-hydroxymethylation nucleotide
<220> FEATURE:
<221> NAME/KEY: modified_base
<222> LOCATION: (4)..(4)
<223> OTHER INFORMATION: 2-Prime-hydroxymethylation nucleotide
<220> FEATURE:
<221> NAME/KEY: modified_base
<222> LOCATION: (6)..(10)
<223> OTHER INFORMATION: 2-Prime-hydroxymethylation nucleotides
<220> FEATURE:
<221> NAME/KEY: modified_base
```

```
<222> LOCATION: (12)..(15)
<223> OTHER INFORMATION: 2-Prime-hydroxymethylation nucleotides
<220> FEATURE:
<221> NAME/KEY: modified_base
<222> LOCATION: (17)..(17)
<223> OTHER INFORMATION: 2-Prime-hydroxymethylation nucleotide
<220> FEATURE:
<221> NAME/KEY: misc_feature
<222> LOCATION: (20)..(21)
<223> OTHER INFORMATION: Thymidine

<400> SEQUENCE: 2
caguguucuu gcucuauaan n                                                    21

<210> SEQ ID NO 3
<211> LENGTH: 21
<212> TYPE: RNA
<213> ORGANISM: Artificial sequence
<220> FEATURE:
<223> OTHER INFORMATION: The sequence is artificially synthesized
<220> FEATURE:
<221> NAME/KEY: modified_base
<222> LOCATION: (2)..(2)
<223> OTHER INFORMATION: 2-Prime-hydroxymethylation nucleotide
<220> FEATURE:
<221> NAME/KEY: modified_base
<222> LOCATION: (4)..(4)
<223> OTHER INFORMATION: 2-Prime-hydroxymethylation nucleotide
<220> FEATURE:
<221> NAME/KEY: modified_base
<222> LOCATION: (9)..(9)
<223> OTHER INFORMATION: 2-Prime-hydroxymethylation nucleotide
<220> FEATURE:
<221> NAME/KEY: modified_base
<222> LOCATION: (15)..(15)
<223> OTHER INFORMATION: 2-Prime-hydroxymethylation nucleotide
<220> FEATURE:
<221> NAME/KEY: misc_feature
<222> LOCATION: (20)..(21)
<223> OTHER INFORMATION: Thymidine

<400> SEQUENCE: 3
uuauagagca agaacacugn n                                                    21

<210> SEQ ID NO 4
<211> LENGTH: 21
<212> TYPE: RNA
<213> ORGANISM: Artificial Sequence
<220> FEATURE:
<223> OTHER INFORMATION: The sequence is artificially synthesized
<220> FEATURE:
<221> NAME/KEY: misc_feature
<222> LOCATION: (20)..(21)
<223> OTHER INFORMATION: Thymidine

<400> SEQUENCE: 4
gcgaaauacc aguggcuuan n                                                    21

<210> SEQ ID NO 5
<211> LENGTH: 21
<212> TYPE: RNA
<213> ORGANISM: Artificial sequence
<220> FEATURE:
<223> OTHER INFORMATION: The sequence is artificially synthesized
<220> FEATURE:
<221> NAME/KEY: misc_feature
<222> LOCATION: (20)..(21)
<223> OTHER INFORMATION: Thymidine

<400> SEQUENCE: 5
gcuacuaaug gaccacuuan n                                                    21
```

-continued

```
<210> SEQ ID NO 6
<211> LENGTH: 21
<212> TYPE: RNA
<213> ORGANISM: Artificial sequence
<220> FEATURE:
<223> OTHER INFORMATION: The sequence is artificially synthesized
<220> FEATURE:
<221> NAME/KEY: misc_feature
<222> LOCATION: (20)..(21)
<223> OTHER INFORMATION: Thymidine

<400> SEQUENCE: 6
caagcagugu guacauugan n                                                    21

<210> SEQ ID NO 7
<211> LENGTH: 21
<212> TYPE: RNA
<213> ORGANISM: Artificial sequence
<220> FEATURE:
<223> OTHER INFORMATION: The sequence is artificially synthesized
<220> FEATURE:
<221> NAME/KEY: misc_feature
<222> LOCATION: (20)..(21)
<223> OTHER INFORMATION: Thymidine

<400> SEQUENCE: 7
ggagacgugg uguugguaan n                                                    21
```

MOLECULAR PROBE FOR NUCLEIC ACID DETECTION, PREPARATION AND USE THEREOF

RELATED APPLICATIONS

The present application is filed pursuant to 35 U.S.C. 371 as a U.S. National Phase application of International Patent Application No. PCT/EP2021/070059, which was filed Jul. 16, 2021, claiming the benefit of Application No. CN 202010691487.8, filed Jul. 17, 2020. The entire text of the aforementioned applications is incorporated herein by reference in its entirety.

SEQUENCE LISTING

The instant application contains a Sequence Listing which has been submitted via Patent Center and is hereby incorporated by reference in its entirety. Said ASCII copy, created on Dec. 26, 2025, is named 766175-GEHT-519US_ST25.txt, and is 3,165 bytes in size.

TECHNICAL FIELD

The disclosure relates to the field of biomolecule detection, and in particular relates to an oligonucleotide molecular probe for in vivo or in vitro nucleic acid detection, and a preparation method and use thereof.

BACKGROUND OF THE INVENTION

Nucleic acid detection technology is widely used in the fields of medical diagnosis, food safety and environmental monitoring. This technique takes, for example, a target nucleic acid derived from a pathogen or a disease as an object of detection, and determines the presence of a pathogen or a disease (e.g., a pathogenic organism, diseased cells or tissues, etc.) by identifying the presence of the target nucleic acid or detecting the level of the target nucleic acid.

The existing nucleic acid detection methods include nucleic acid blotting, microarray, nucleic acid amplification (for example, RT-PCR, RT-LAMP, SAT), etc. However, these methods require nucleic acid extraction, amplification and detection, which involves tedious operation steps and expensive instruments and materials, which makes the detection cost high, time-consuming and laborious. In addition, the selection of conditions and reagents in the operation, as well as the differences in the operation between the operators may also interfere with the nucleic acid from the sample (for example causing its loss or being blocked), resulting in the target nucleic acid from some samples cannot be detected normally, which is easy to produce false negative results.

Nucleic acid probes used for in situ hybridization are increasingly used for the detection of extracellular and intracellular biochemical substances. When the structure of the cell or tissue remains unchanged, the labeled nucleotide fragments, based on the principle of base pairing, can specifically bind (e.g., hybridize) to the corresponding target nucleic acid in the cell or tissue to be tested and are identified via optical detection methods or imaging techniques to enable detection of the target nucleic acid (e.g., visual localization and/or quantification). Probes commonly used for such detections include probes labeled with radionuclides or fluorescence. However, these probes still have limitations in terms of detection accuracy and safety.

Accordingly, there is still a need for a new type of molecular probe, which is convenient to prepare and can provide safe and accurate nucleic acid detection.

BRIEF DESCRIPTION OF THE INVENTION

In one aspect, provided herein is a molecular probe for detection of a nucleic acid, comprising,
- (1) a molecular probe carrier which comprises a cell penetrating peptide and a detectable label coupled to the cell penetrating peptide, and
- (2) a targeting oligonucleotide,
- wherein the targeting oligonucleotide is attached to the molecular probe carrier.

In another aspect, provided herein is a method for preparing a molecular probe, comprising,
- coupling a detectable label to a cell penetrating peptide to obtain a molecular probe carrier, and
- incubating the molecular probe carrier with the targeting oligonucleotide for a duration of time sufficient to allow attachment between the molecular probe carrier and the targeting oligonucleotide, to obtain the molecular probe.

In another aspect, provided herein is a method for detection of a nucleic acid, comprising,
- applying the molecular probe according to claim 1 to a subject or a sample from the subject, and
- determining the presence and/or level of a target nucleic acid by detecting the detectable marker in the subject or the sample from the subject.

In another aspect, provided herein is a kit for detection of a nucleic acid, comprising,
- a container comprising a molecular probe carrier as defined in claim 1;
- a container comprising a targeting oligonucleotide as defined in claim 1; and
- optionally, instructions for use.

It is found that the molecular probes described herein can be prepared by a one-step method from a molecular probe carrier (i.e., conjugate of a detectable label and a cell penetrating peptide) and a targeting oligonucleotide. Compared with the existing multi-step probe synthesis methods, the method for preparing the molecular probe described herein is simple, efficient, raw material efficient and environmental friendly, and the prepared probe can provide safe and accurate nucleic acid detection.

BRIEF DESCRIPTION OF THE DRAWING

The present disclosure will be further described below with reference to the drawings. The drawings and descriptions provided are merely illustrative of embodiments of the present disclosure, and are not intended to limit the scope of the present disclosure.

FIG. 1 is a scheme showing the preparation of a cell penetrating peptide-VSP molecular probe carrier.

FIG. 2d shows the fluorescence density curves of the group transfected with TTR-targeting siRNA, the group transfected with NC-siRNA as negative control and the untransfected group as blank control at different time points.

DETAILED DESCRIPTION OF THE INVENTION

Figure 2:
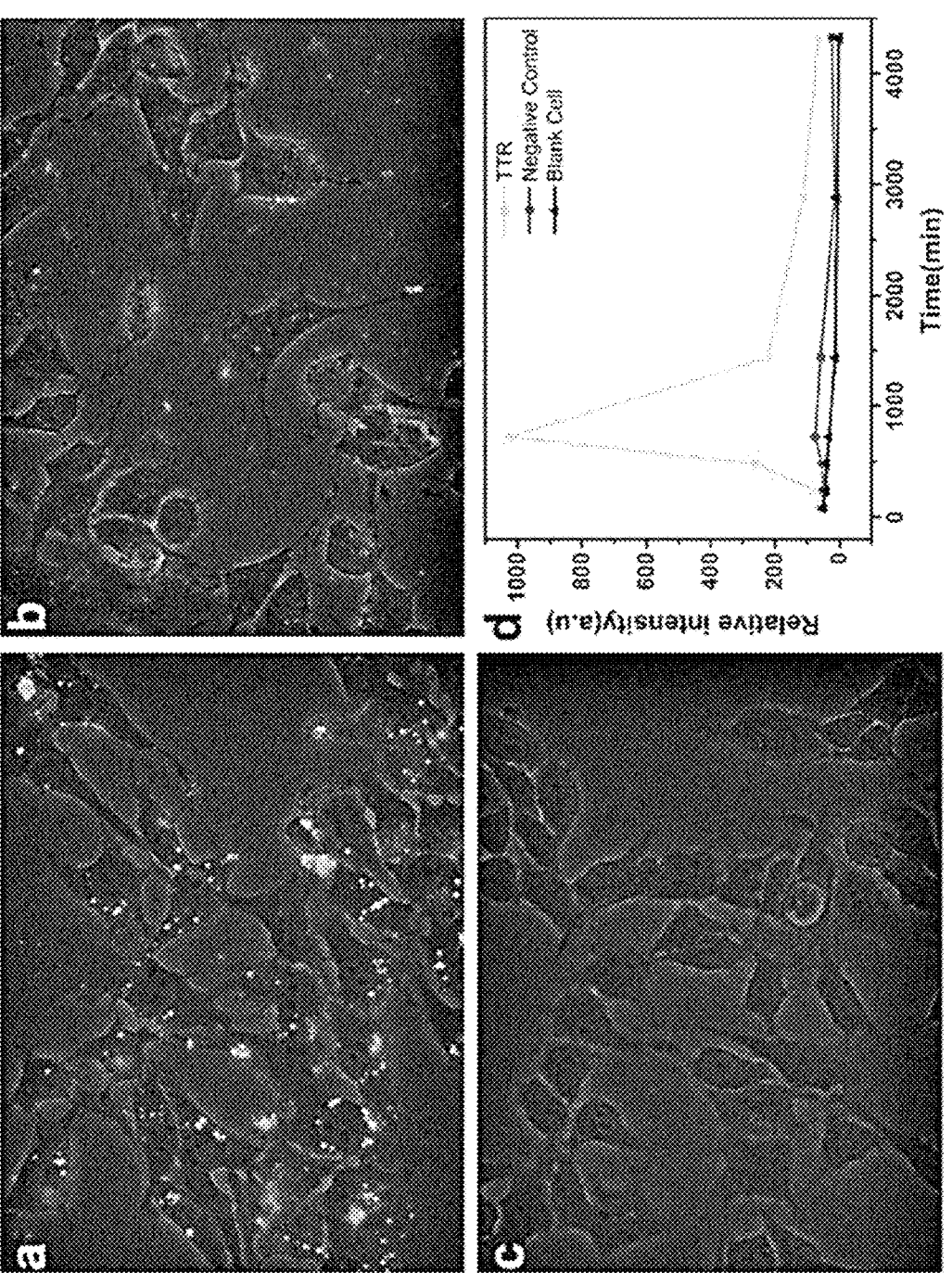
FIG. 2 shows the experimental verification of the effect of TTR-targeting siRNA targeting TTR mRNA. Panels 2a, 2b and 2c show the results of fluorescence imaging of rat hepatocytes BRL3A 12 hours after transfection in vitro. Panel 2a shows the result of transfection with TTR-targeting siRNA. Panel 2b shows the result of transfection with NC-siRNA as negative control. Panel 2c shows the result of untransfected cells as blank control.

The meaning of scientific and technical terms in this disclosure is consistent with the general understanding in the art unless otherwise stated. In this disclosure, "a/an" or its combination with various quantifiers includes both singular and plural meanings unless specifically stated otherwise. In the disclosure, when multiple values, ranges of values, or combinations thereof are given for the same parameter or variable, it is equivalent to specifically disclose these values, end values of the ranges, and ranges formed by any two of these values. Whether or not any numerical value is modified by a modifier such as "about", it covers the approximate range that can be understood by those skilled in the art, such as plus or minus 10%, 5%, and so on. In this disclosure, each "embodiment" refers equally to and covers the implementation of the methods and systems of the present application. One or more technical features in any embodiment can be freely combined with one or more technical features in any one or more other embodiments, and the embodiments obtained thereby also belong to the content disclosed in this application.

In one aspect, provided herein is a molecular probe for detection of a nucleic acid, comprising, (1) a molecular probe carrier which comprises a cell penetrating peptide and a detectable label coupled to the cell penetrating peptide, and (2) a targeting oligonucleotide, wherein the targeting oligonucleotide is attached to the molecular probe carrier.

In some embodiments, the molecular probes described herein can be oligonucleotide molecular probes.

In some embodiments, the nucleic acid detection can be nucleic acid detection in vitro. In some embodiments, the nucleic acid detection can be nucleic acid detection in vitro in a cell comprising sample. In other embodiments, the nucleic acid detection can be detection in vivo.

The molecular probe described herein comprises a cell penetrating peptide. As used herein, the term "cell penetrating peptide" (also referred to herein as "CP") refers to a class of short peptides that can promote cellular uptake of various molecular cargoes (from nanoparticles to small chemical molecules and large fragments of DNA). They have the function of delivering the cargo into the cell.

In some embodiments, the cell penetrating peptide can comprise the amino acid sequence set forth in SEQ ID NO: 1.

In one embodiment, the cell penetrating peptide can comprise an amino acid sequence comprising one or two amino acid mutations at any one or two positions in the amino acid sequence set forth in SEQ ID NO: 1. In a specific embodiment, the cell penetrating peptide can comprise an amino acid sequence comprising one or two amino acid mutations at any one or two positions of the amino acid sequence set forth in SEQ ID NO: 1, wherein the lysine residue in SEQ ID NO: 1 remains unchanged. The amino acid mutation is selected from the group consisting of addition, substitution, deletion, and a combination thereof. The amino acid mutation(s) can occur at the same or different positions at either end, both ends, or within the amino acid sequence set forth in SEQ ID NO: 1.

In some embodiments, the length of the cell penetrating peptide can range from 8 to 12 amino acids. In some alternative embodiments, the length of the cell penetrating peptide can be within a range formed by taking any two of 8, 9, 10, 11, and 12 as the end points.

In some embodiments, the cell penetrating peptide can comprise an amino acid sequence having at least 80%, at least 90%, or 100% sequence identity with the amino acid sequence set forth in SEQ ID NO: 1. In some embodiments, the cell penetrating peptide consists of the amino acid sequence set forth in SEQ ID NO: 1.

In some embodiments, the cell penetrating peptide can be a cyclic peptide. The cyclic peptide can be formed by connecting the first and last amino acid residues of the amino acid sequence of the cell penetrating peptide.

The cell penetrating peptides described herein can be obtained according to polypeptide synthesis and/or modification methods known in the art.

The molecular probe described herein further comprises a detectable label. As used herein, the term "detectable label" refers to a substance capable of generating or enhancing a signal for detection.

In some embodiments, the detectable label can be a contrast agent. As used herein, the term "contrast agent" refers to a substance that is introduced into a site to be measured (such as in cells, tissues, or organs) to form an image or enhance the imaging effect. In some cases, "contrast agent" may also be referred to as "imaging agent".

In some embodiments, the contrast agent can comprise a CT contrast agent. The CT contrast agent can be used as a detectable label for electronic computed tomography (CT) detection. In some embodiments, the CT contrast agent can comprise one or more selected from the group consisting of iodixanol, iohexol, iopamidol, iopromide and ioversol. In some embodiments, the contrast agent can be iodixanol. The term "iodixanol" in this disclosure can used interchangeably with its trade name "Visipaque" (VSP for short), which as a non-ionic contrast agent containing six iodine disomes can be used in a CT detection.

In general, iodixanol has the structure represented by the following formula (I):

(I)

In some embodiments, the detectable marker can also comprise other contrast agents, for example, one or more contrast agents selected from MRI contrast agents (e.g., USPIO), fluorescent contrast agents (e.g., 5-FAM SE), and radioactive contrast agents (e.g., Positron nuclide 18F or 68Ga).

The detectable label described herein can be coupled directly or indirectly via a linker to the cell penetrating peptide.

In some embodiments, the detectable label described herein can be coupled to the cell penetrating peptide in a covalent manner. In some embodiments, the detectable label can be coupled to the cell penetrating peptide via an amide bond. In some embodiments, the detectable label can be coupled to an amino group on an amino acid residue comprised in the cell penetrating peptide. In a specific embodiment, the detectable label is coupled to a lysine residue (e.g., an amino group on the lysine residue) comprised in the cell penetrating peptide. In some embodiments, the detectable label can be coupled indirectly via a linker to the cell penetrating peptide. In some embodiments, the linker can comprise an alkylenecarbonyl group. In some embodiments, the alkylenecarbonyl group can be a $C_1$-$C_{12}$ alkylenecarbonyl group, for example, a $C_1$-$C_{10}$ alkylenecarbonyl group, a $C_1$-$C_8$ alkylenecarbonyl group, a $C_1$-$C_6$ alkylenecarbonyl group, or a $C_1$-$C_4$ alkylenecarbonyl group. As used herein, "alkylene" refers to linear alkylene, branched alkylene, or cycloalkylene, preferably linear alkylene. For example, "$C_1$-$C_{12}$ alkylene" as described herein refers to an alkylene group comprising the indicated number (1 to 12) of carbon atoms.

In an exemplary embodiment where the detectable label is VSP, the VSP can be coupled to the cell penetrating peptide through an amide bond. In some embodiments, the VSP can be coupled to an amino group on an amino acid residue comprised in the cell penetrating peptide. In some embodiments, the VSP can be coupled to an amino group on an amino acid residue comprised in the cell penetrating peptide. In a specific embodiment, the VSP is coupled to a lysine residue (e.g., an amino group on the lysine residue) comprised in the cell penetrating peptide. In some embodiments, the VSP can be coupled indirectly via a linker to the cell penetrating peptide. In some embodiments, the linker can comprise an alkylenecarbonyl group. In some embodiments, the alkylenecarbonyl group is a $C_1$-$C_{12}$ alkylenecarbonyl group, for example, a $C_1$-$C_{10}$ alkylenecarbonyl group, a $C_1$-$C_8$ alkylenecarbonyl group, a $C_1$-$C_6$ alkylenecarbonyl group, or a $C_1$-$C_4$ alkylenecarbonyl group. In an exemplary embodiment, the VSP is coupled to the cell penetrating peptide via a linker comprising —$(CH_2)_n$CO—, where n is an integer of from 1 to 10. In a more specific embodiment, the VSP and the cell penetrating peptide can be coupled in the following manner: [VSP]-$(CH_2)_n$CO-[cell penetrating peptide], where n is an integer of from 1 to 10. In some alternative embodiments, n can be an integer of from 1 to 8. In some alternative embodiments, n can be an integer of from 1 to 6, specifically from 1 to 4, more specifically 2, 3 or 4.

In the present disclosure, a detectable label coupled to a cell penetrating peptide may also be referred to herein as a "probe carrier" or "molecular probe carrier", which is used for further attachment of a targeting oligonucleotide.

The molecular probe described herein also comprises a targeting oligonucleotide. As used herein, the term "targeting oligonucleotide" refers to a short nucleic acid sequence that targets (e.g., be complementary) to a target gene (e.g., target site within a target nucleic acid or target gene) and is up to 100 (e.g., 10 to 80, 10 to 50, 10 to 40) bases in length. The targeting oligonucleotides described herein include deoxyribonucleic acid (DNA) and/or ribonucleic acid (RNA). The targeting oligonucleotide described herein can be a single-stranded oligonucleotide or a double-stranded oligonucleotide.

In some embodiments, the targeting oligonucleotide is an oligonucleotide that can specifically bind to a unique target site of a pathogenic microorganism (e.g., the genome of a pathogenic microorganism), for example, an oligonucleotide that is specifically complementary to a target site of the genome of a pathogenic microorganism genome. The pathogenic microorganisms include, but are not limited to, viruses, mycoplasmas, chlamydia, bacteria, and fungi. In further embodiments, the targeting oligonucleotide is an oligonucleotide that targets to a disease- or disorder-specific target site. The disease or disorder is usually characterized by abnormal activity (e.g., overexpression) of one or more biomolecules or abnormal activity of a variant of one or more biomolecules, including but not limited to: precancerous disorders, cancer, tissue fibrosis, inflammatory diseases, genetic diseases, dysplasia, etc.

In some embodiments, the targeting oligonucleotide can be siRNA or shRNA. In some embodiments, the targeting oligonucleotide can be siRNA.

In an exemplary embodiment, the targeting oligonucleotide can be a siRNA targeting to a specific site in the transthyretin (TTR) gene, which may also be referred to herein as "TTR targeting siRNA." In a specific embodiment, the TTR targeting siRNA can comprise a sense strand comprising the nucleotide sequence set forth in SEQ ID NO: 2. In a more specific embodiment, the TTR-targeting siRNA can comprise a sense strand comprising the methylated nucleotide sequence set forth in SEQ ID NO: 2. For example, the methylated nucleotide sequence set forth in SEQ ID NO: 2 can be 5'-mCAGmUGmUmUmCmU-mUGmCmUmCmUAmUAAdTdT-3', where m represents 2' hydroxymethylation of the corresponding base. In a specific embodiment, the TTR-targeting siRNA can comprise an antisense strand comprising the nucleotide sequence set forth in SEQ ID NO: 3. In a more specific embodiment, the TTR-targeting siRNA can comprise an antisense strand comprising the methylated nucleotide sequence set forth in SEQ ID NO: 3. For example, the methylated nucleotide sequence set forth in SEQ ID NO: 3 can be 5'-UmUAmUA-GAGmCAAGAAmCACUGdTdT-3', where m represents 2' hydroxymethylation of the corresponding base.

In a specific embodiment, the TTR-targeting siRNA can comprise a sense strand comprising the nucleotide sequence set forth in SEQ ID NO: 2 and an antisense strand comprising the nucleotide sequence set forth in SEQ ID NO: 3.

In an exemplary embodiment, the targeting oligonucleotide is a siRNA targeting to a specific site in the gene of the new coronavirus (SARS-CoV-2) (also called "new corona-virus" or "2019-nCov"), which may also be referred to herein as "new coronavirus-targeting siRNA" or "SARS-CoV-2 targeting siRNA." In a specific embodiment, the SARS-CoV-2 targeting siRNA can comprise a sense strand comprising the nucleotide sequence set forth in SEQ ID NO: 4. In another specific embodiment, the SARS-CoV-2 targeting siRNA can comprise a sense strand comprising the nucleotide sequence set forth in SEQ ID NO: 5.

In an exemplary embodiment, the targeting oligonucleotide is a siRNA targeting to a specific site in the gene of the influenza A virus (IAV), which may also be referred to herein as an "IAV targeting siRNA." In a specific embodiment, the IAV targeting siRNA can comprise a sense strand comprising the nucleotide sequence set forth in SEQ ID NO: 6. In another specific embodiment, the IAV targeting siRNA can comprise a sense strand comprising the nucleotide sequence set forth in SEQ ID NO: 7. The exemplified IAV targeting siRNAs are siRNAs that have broad-spectrum antiviral activity against specific sites designed for highly conserved sequences in influenza A virus genes.

In some embodiments, the targeting oligonucleotide can be attached to the molecular probe carrier via covalent or non-covalent interactions. In some embodiments, the targeting oligonucleotide can be attached to the molecular probe carrier via non-covalent interaction.

In another aspect, provided herein is a method for preparing a molecular probe, comprising, coupling a detectable label to a cell penetrating peptide to obtain a molecular probe carrier, and incubating the molecular probe carrier with the targeting oligonucleotide for a duration of time sufficient to allow attachment between the molecular probe carrier and the targeting oligonucleotide, to obtain the molecular probe.

The method for preparing the molecular probe as described herein can comprise providing a cell penetrating peptide.

In some embodiments, the cell penetrating peptide can comprise the amino acid sequence set forth in SEQ ID NO: 1.

In one embodiment, the cell penetrating peptide can comprise an amino acid sequence comprising one or two amino acid mutations at any one or two positions in the amino acid sequence set forth in SEQ ID NO: 1. In a specific embodiment, the cell penetrating peptide can comprise an amino acid sequence comprising one or two amino acid mutations at any one or two positions of the amino acid sequence set forth in SEQ ID NO: 1, wherein the lysine residue in SEQ ID NO: 1 remains unchanged. The amino acid mutation is selected from the group consisting of addition, substitution, deletion, and a combination thereof. The amino acid mutation(s) can occur at the same or different positions at either end, both ends, or within the amino acid sequence set forth in SEQ ID NO: 1.

In some embodiments, the length of the cell penetrating peptide can range from 8 to 12 amino acids. In some alternative embodiments, the length of the cell penetrating peptide can be within a range formed by taking any two of 8, 9, 10, 11, and 12 as the end points.

In some embodiments, the cell penetrating peptide can comprise an amino acid sequence having at least 80%, at least 90%, or 100% sequence identity with the amino acid sequence set forth in SEQ ID NO: 1. In some embodiments, the cell penetrating peptide consists of the amino acid sequence set forth in SEQ ID NO: 1.

In some embodiments, the cell penetrating peptide can be a cyclic peptide. The cyclic peptide can be formed by connecting the first and last amino acid residues of the amino acid sequence of the cell penetrating peptide.

The cell penetrating peptides described herein can be obtained according to polypeptide synthesis and/or modification methods known in the art.

The method for preparing the molecular probe as described herein can comprise providing a detectable label. In an embodiment, the detectable label can be a contrast agent.

In some embodiments, the contrast agent can comprise a CT contrast agent. In some embodiments, the CT contrast agent can comprise one or more selected from the group consisting of iodixanol, iohexol, iopamidol, iopromide and ioversol. In some embodiments, the contrast agent can be iodixanol (VSP).

In some embodiments, the detectable marker can also comprise other contrast agents, for example, one or more contrast agents selected from MRI contrast agents (e.g., USPIO), fluorescent contrast agents (e.g., 5-FAM SE), and radioactive contrast agents (e.g., Positron nuclide 18F or 68Ga).

In some cases, the method for preparing the molecular probes as described herein can further comprise modifying the detectable label so that the modified detectable label has a moiety for coupling to the cell penetrating peptide. In some embodiments, the coupling can be a covalent coupling.

In some embodiments, the moiety for coupling to the cell penetrating peptide can comprise a carboxyl group. In some embodiments, the moiety for coupling to the cell penetrating peptide can comprise an alkylenecarboxyl group. In some embodiments, the alkylenecarbonyl group can be a $C_1$-$C_{12}$ alkylenecarbonyl group, for example, a $C_1$-$C_{10}$ alkylenecarbonyl group, a $C_1$-$C_8$ alkylenecarbonyl group, a $C_1$-$C_6$ alkylenecarbonyl group, or a $C_1$-$C_4$ alkylenecarbonyl group.

In an exemplary embodiment where the detectable label is VSP, the VSP can be modified to comprise a moiety for coupling to a cell penetrating peptide. In some embodiments, the moiety for coupling to the cell penetrating peptide can comprise a carboxyl group. In some embodiments, the moiety for coupling to the cell penetrating peptide can comprise an alkylenecarboxyl group. In some embodiments, the alkylenecarbonyl group can be a $C_1$-$C_{12}$ alkylenecarbonyl group, for example, a $C_1$-$C_{10}$ alkylenecarbonyl group, a $C_1$-$C_8$ alkylenecarbonyl group, a $C_1$-$C_6$ alkylenecarbonyl group, or a $C_1$-$C_4$ alkylenecarbonyl group. In some embodiments, the VSP can be modified to comprise a moiety for coupling to a cell penetrating peptide, wherein the moiety comprises —$(CH_2)_n$COOH, where n is an integer of from 1 to 10. In some alternative embodiments, n can be an integer of from 1 to 8. In some alternative embodiments, n can be an integer of from 1 to 6, specifically from 1 to 4, and more specifically 2, 3, or 4.

In an exemplary embodiment, the modified VSP has the structure represented by the following formula (II):

In some embodiments, the detectable label and the cell penetrating peptide can be coupled by mixing or incubating the two. In some embodiments, the mixing or incubation can be performed for a duration of time, for example, 1 to 4 hours, for example 1 to 3 hours, for example 2 to 3 hours.

(II)

The method for preparing the molecular probe as described herein further comprises coupling a detectable label to a cell penetrating peptide to obtain a molecular probe carrier.

In some embodiments, the detectable label described herein can be coupled to the cell penetrating peptide in a covalent manner. In some embodiments, the detectable label can be coupled to the cell penetrating peptide via an amide bond. In some embodiments, the detectable label can be coupled to the cell penetrating peptide by forming an amide bond between a carboxyl group on the detectable label and an amino group on an amino acid residue comprised in the cell penetrating peptide. In a specific embodiment, the detectable label is coupled to a lysine residue comprised in the cell penetrating peptide.

In an exemplary embodiment in which the detectable label is a VSP modified to comprise a moiety (e.g., a carboxyl-containing moiety) for coupling to a cell penetrating peptide, the modified VSP can be coupled to the cell penetrating peptide via an amide bond. In some embodiments, the modified VSP can be coupled to the cell penetrating peptide by forming an amide bond between a carboxyl group on the VSP and an amino group on an amino acid residue comprised in the cell penetrating peptide. In some embodiments, the modified VSP can be coupled to a lysine residue comprised in the cell penetrating peptide. In an exemplary embodiment, the modified VSP can be coupled to the cell penetrating peptide through a moiety for coupling to the cell penetrating peptide, such as $-(CH_2)_n$ COOH, where n is an integer of from 1 to 10, to an amino group on the lysine residue comprised in the cell penetrating peptide. In some alternative embodiments, n can be an integer of from 1 to 8. In some alternative embodiments, n can be an integer of from 1 to 6, specifically from 1 to 4, and more specifically 2, 3, or 4.

In some cases, before coupling the detectable label to the cell penetrating peptide, the method as described herein can further comprise activating the terminal carboxyl group of the detectable label. In some exemplary embodiments, the activation can utilize 1-(3-dimethylaminopropyl)-3-ethyl-carbodiimide hydrochloride (EDC) and N-hydroxythiosuccinimide (Sulfo-NHS).

In some embodiments, the mixing or incubation can be performed at room temperature. In some embodiments, the detectable marker and the cell penetrating peptide can be mixed at a molar ratio of 3:1 to 1:3, for example, 2.5:1 to 1:2.5, 2:1 to 1:2, 1:1.5 to 1.5:1 or 1:1.

In some cases, the method for preparing the molecular probe as described herein can further comprise separating the detectable label coupled to the cell penetrating peptide as a molecular probe carrier from the mixed reaction of the detectable label and the cell penetrating peptide. In some embodiments, the separation can be performed by a separation method selected from centrifugal separation and HPLC separation.

The method for preparing the molecular probe as described herein further comprises incubating the molecular probe carrier with the targeting oligonucleotide for a duration of time sufficient to allow attachment between the molecular probe carrier and the targeting oligonucleotide, to obtain the molecular probe.

In some embodiments, the targeting oligonucleotide can be attached to the molecular probe carrier via covalent or non-covalent interactions. In some embodiments, the targeting oligonucleotide can be attached to the molecular probe carrier via non-covalent interaction.

The targeting oligonucleotide can be a single-stranded oligonucleotide or a double-stranded oligonucleotide.

In some embodiments, the targeting oligonucleotide is an oligonucleotide that can specifically bind to a unique target site of a pathogenic microorganism (e.g., the genome of a pathogenic microorganism), for example, an oligonucleotide that is specifically complementary to a target site of the genome of a pathogenic microorganism genome. The pathogenic microorganisms include, but are not limited to, viruses, mycoplasmas, chlamydia, bacteria, and fungi. In further embodiments, the targeting oligonucleotide is an oligonucleotide that targets to a disease- or disorder-specific target site. The disease or disorder is usually characterized by abnormal activity (e.g., overexpression) of one or more biomolecules or abnormal activity of a variant of one or more biomolecules, including but not limited to: precancerous disorders, cancer, tissue fibrosis, inflammatory diseases, genetic diseases, dysplasia, etc.

In some embodiments, the targeting oligonucleotide can be siRNA or shRNA. In some embodiments, the targeting oligonucleotide can be siRNA.

In an exemplary embodiment, the targeting oligonucleotide can be a TTR targeting siRNA. In a specific embodiment, the TTR targeting siRNA can comprise a sense strand comprising the nucleotide sequence set forth in SEQ ID NO: 2. In a more specific embodiment, the TTR-targeting siRNA can comprise a sense strand comprising the methylated nucleotide sequence set forth in SEQ ID NO: 2. For example, the methylated nucleotide sequence set forth in SEQ ID NO: 2 can be 5'-mCAGmUGmUmUmCmU-mUGmCmUmCmUAmUAAdTdT-3', where m represents 2' hydroxymethylation of the corresponding base. In a specific embodiment, the TTR-targeting siRNA can comprise an antisense strand comprising the nucleotide sequence set forth in SEQ ID NO: 3. In a more specific embodiment, the TTR-targeting siRNA can comprise an antisense strand comprising the methylated nucleotide sequence set forth in SEQ ID NO: 3. For example, the methylated nucleotide sequence set forth in SEQ ID NO: 3 can be 5'-UmUAmUA-GAGmCAAGAAmCACUGdTdT-3', where m represents 2' hydroxymethylation of the corresponding base.

In a specific embodiment, the TTR-targeting siRNA can comprise a sense strand comprising the nucleotide sequence set forth in SEQ ID NO: 2 and an antisense strand comprising the nucleotide sequence set forth in SEQ ID NO: 3.

In an exemplary embodiment, the targeting oligonucleotide can be a SARS-CoV-2 targeting siRNA. In a specific embodiment, the SARS-CoV-2 targeting siRNA can comprise a sense strand comprising the nucleotide sequence set forth in SEQ ID NO: 4. In another specific embodiment, the SARS-CoV-2 targeting siRNA can comprise a sense strand comprising the nucleotide sequence set forth in SEQ ID NO: 5.

In an exemplary embodiment, the targeting oligonucleotide can be an IAV targeting siRNA. In a specific embodiment, the IAV targeting siRNA can comprise a sense strand comprising the nucleotide sequence set forth in SEQ ID NO: 6. In another specific embodiment, the IAV targeting siRNA can comprise a sense strand comprising the nucleotide sequence set forth in SEQ ID NO: 7.

In some embodiments, the molecular probe carrier and the targeting oligonucleotide can be mixed in a molar ratio of 5:1 to 30:1, for example, 10:1 to 25:1, 15:1 to 20:1, for incubation. In some embodiments, the mixing medium can be an aqueous liquid, for example, pure water or an aqueous solution (such as cell culture medium). In some embodiments, the incubation is performed at ambient temperature (for example, room temperature conditions, for example 15° C. to 25° C.). In some embodiments, the incubation lasts for 10 to 30 minutes, for example, 10 to 20 minutes, for example, 15 to 20 minutes.

In some embodiments, the molecular probes obtained after incubation can be used directly without further purification.

In some embodiments, the molecular probe can be prepared for in vivo or in vitro nucleic acid detection.

In some embodiments, the molecular probe carrier (e.g., the detectable label coupled to a cell penetrating peptide as described herein) can be prepared using a one-step method.

In some embodiments, the incubation of the molecular probe carrier with the targeting oligonucleotide can be performed immediately before detection. In some embodiments, the molecular probes described herein can be prepared from the molecular probe carrier (i.e., the detectable label coupled to the cell penetrating peptide as described herein) and the targeted target nucleotide by a one-step method.

Compared with the existing multi-step probe synthesis methods, the method for preparing the molecular probe as described herein is simple, efficient, raw material efficient and environmental friendly. The method described in this article has good practicability and is suitable for mass production of molecular probes.

In another aspect, provided herein is a method for detection of a nucleic acid, comprising, applying the molecular probe according to claim 1 to a subject or a sample from the subject, and determining the presence and/or level of a target nucleic acid by detecting the detectable marker in the subject or the sample from the subject.

In some embodiments, the subject is an animal, such as a mammal, such as a human.

In some embodiments, the nucleic acid detection can be an in vivo nucleic acid detection. In some embodiments, the molecular probe can be administered by one or more ways selected from injection (such as intramuscular injection, intravenous injection, etc.), oral administration, and inhalation (such as aerosol inhalation). In some embodiments, the molecular probe can be administered by aerosol inhalation. In some embodiments, the molecular probe can be administered in an amount ranging from 6.5 to 32.5 mg/kg of the subject's body weight. In some embodiments, the detection can be performed 1 to 4 hours, preferably 2 to 3 hours after administration of the molecular probe.

In some embodiments, the detection can include, but is not limited to, CT detection, MRI detection, fluorescence detection, radionuclide detection, and the like. In some embodiments, the detection is CT detection.

In some embodiments, the detection can be an in vitro nucleic acid detection. In some embodiments, the sample from the subject is an ex vivo cell-containing sample taken from the subject, for example, cell-containing tissues or cell populations (e.g., biopsies, tissue specimens, cell suspensions, etc.) In some embodiments, the ex vivo cell-containing sample can be a single cell suspension or the culture of adherent cells. In some embodiments, administration of the molecular probe can comprise contacting (for example, incubating) the sample from the subject with the molecular probe described herein. In the embodiment where the ex vivo cell-containing sample is the culture of adherent cells, the molecular probe can be added when the cells are confluent by 30% to 80%, preferably 40% to 70%. In some embodiments, after the molecular probe is added, the sample is incubated with the molecular probe under conditions suitable for cell culture (e.g., 37° C., 5% $CO_2$). In some embodiments, the incubation process can be carried out for 12 to 36 hours, for example 12 to 24 hours, for example 18 to 24 hours.

In some embodiments, the method can further comprise, optionally, after the incubation is completed, half-volume exchanging the cell culture medium (for example, cell culture medium containing 20% fetal bovine serum) for the cells. As used herein, "half-volume exchange" or "half-volume exchanging" the cell culture medium refers to replacing half of the old medium with the fresh medium for the cell culture. In some embodiments, the detection can be performed 80 minutes to 72 hours, for example, 4 to 48 hours, for example 4 to 24 hours, for example 8 to 12 hours after the completion of the incubation.

In some embodiments, the method can further comprise, optionally, washing the cells before detection, to remove molecular probes that are not bound to the target gene and are excreted by the cells. In some embodiments, the washing can be performed 2 to 3 times with PBS or cell culture medium (e.g., cell culture medium containing 20% fetal bovine serum).

In some embodiments, the method can further comprise, before administering the molecular probe, preparing the molecular probe from the molecular probe carrier and the targeting oligonucleotide as described herein.

In some embodiments, the preparation of the molecular probe from the molecular probe carrier and the targeting oligonucleotide described herein can be accomplished by a one-step method, that is, the preparation of the molecular probe can be performed by mixing and incubating the molecular probe carrier with the targeting oligonucleotide, and the so obtained molecular probe can be used for detection without further processing.

In some embodiments, the molecular probe carrier can comprise a detectable label coupled to the cell penetrating peptide as described above. In some embodiments, the method can comprise mixing the molecular probe carrier and the targeting oligonucleotide in a molar ratio of 5:1 to 30:1, for example, 10:1 to 25:1, 15:1 to 20:1, for incubation. In some embodiments, the mixing medium can be an aqueous liquid, for example, pure water or an aqueous solution (such as cell culture medium). In some embodiments, the incubation can be performed at ambient temperature (for example, room temperature conditions, for example, 15° C. to 25° C.). In some embodiments, the incubation lasts for 10 to 30 minutes, for example, 10 to 20 minutes, for example, 15 to 20 minutes.

The method for detection of a nucleic acid provided herein allows molecular probes to be made from molecular probe carriers and targeting oligonucleotides by a one-step method immediately before detection. The preparation of the molecular probe is convenient and safe, and the prepared molecular probe can be used for detection without further processing.

Further, compared with the probes currently used for nucleic acid detection (such as probes with radionuclides or fluorescent labels), the probes provided herein are causing little radioactive contamination and are less background disturbing, thus can provide improved detection accuracy.

In another aspect, provided herein is a kit for detection of a nucleic acid, comprising, a container comprising a molecular probe carrier as defined in claim 1;

a container comprising a targeting oligonucleotide as defined in claim 1; and optionally, instructions for use.

In some embodiments, the kit can be used for in vivo detection. In other embodiments, the kit can be used for in vitro detection.

In some embodiments, the targeting oligonucleotide can be in a ready-to-use solution (which can be used directly without further dilution), concentrated solution, or lyophilized form.

In some embodiments, the molecular probe carrier can be in a ready-to-use solution (which can be used directly without further dilution), concentrated solution, or lyophilized form.

In some alternative embodiments, the kit can further comprise a medium for mixing the molecular probe carrier and the targeting oligonucleotide, for example, an aqueous liquid, for example pure water or an aqueous solution (such as cell culture medium). In some alternative embodiments, the kit can further comprise one or more devices (e.g., one or more containers) for diluting and/or mixing the molecular probe carrier and/or the targeting oligonucleotide.

EXAMPLES

The technical solutions described herein are further described below in conjunction with specific examples. It should be understood that these examples are only used to illustrate the principle of the present disclosure and the effect thereof, and should not be construed as to limit the present disclosure. The above examples can all be modified and altered by those skilled in the art, without departing from the spirit and scope of the present disclosure as defined in the following appended claims.

Unless otherwise stated, percentages and parts are calculated by weight. Unless otherwise defined, all professional and scientific terms used herein may have the same meanings as the meanings well known by those skilled in the art. In addition, any methods and materials similar to or equivalent to those described herein can be applied to the technical solutions of the present disclosure. The preferred embodiments and examples described herein are for demonstration purposes only.

Example 1: Preparation of Cell Penetrating Peptide-VSP Molecular Probe Carrier It is found through research that, compared with linear cell penetrating peptides, circular cell penetrating peptides can provide better cell transfection. In the following illustrative example, a cyclic peptide having an amino acid sequence as set forth in SEQ ID NO: 1 (hereinafter abbreviated as "CP") was used as a cell penetrating peptide for the following experiments.

In this example, the contrast agent VSP-320 (GE Healthcare, Catalog No.: 1181607 CHN) was used as a detectable label.

A). VSP Structure and Modification

The VSP-320 used in this example has the structure shown in the following formula (I):

(I)

The VSP-320 of formula (I) was modified to comprise a carbon chain with a carboxyl group at the end to form a modified Visipaque (cVSP) having the structure shown by the following formula (II):

(II)

B). 1-(3-dimethylaminopropyl)-3-ethylcarbodiimide hydrochloride (EDC, SIGMA, Catalog No.: E7750) and N-hydroxythiosuccinimide (sulfo-NHS, SIGMA, Catalog No.: 56485) were used to activate the terminal carboxyl group of cVSP, by using the following process:

a. To 1 mL of cVSP solution (10 mg/mL), 11.93 mg of DEC (final concentration 0.0623 mM/mL) and then 32.58 mg of sulfo-NHS (final concentration 0.156 mM/mL) were added;

b. The mixture was thoroughly mixed and reacted at room temperature for 15 minutes;

c. To the reaction solution, concentrated PBS (10×) was added to increase the pH of the buffer to above 7.0 to stop the above reaction;

C). The probe carrier was obtained by reacting the amino group in the lysine in the cyclic peptide with the terminal activated cVSP, using the following process:

a. 6.85 mg of the cyclic peptide was added to the reaction solution of B).c above, and the solution was mixed thoroughly and reacted at room temperature for 2 hrs;

b. After the reaction was completed, 0.33 mg of hydroxylamine was added to the above solution to make the final concentration 10 mM to quench the reaction;

D). The final product VSP-CP was separated from the reaction by HPLC.

Figure 1:
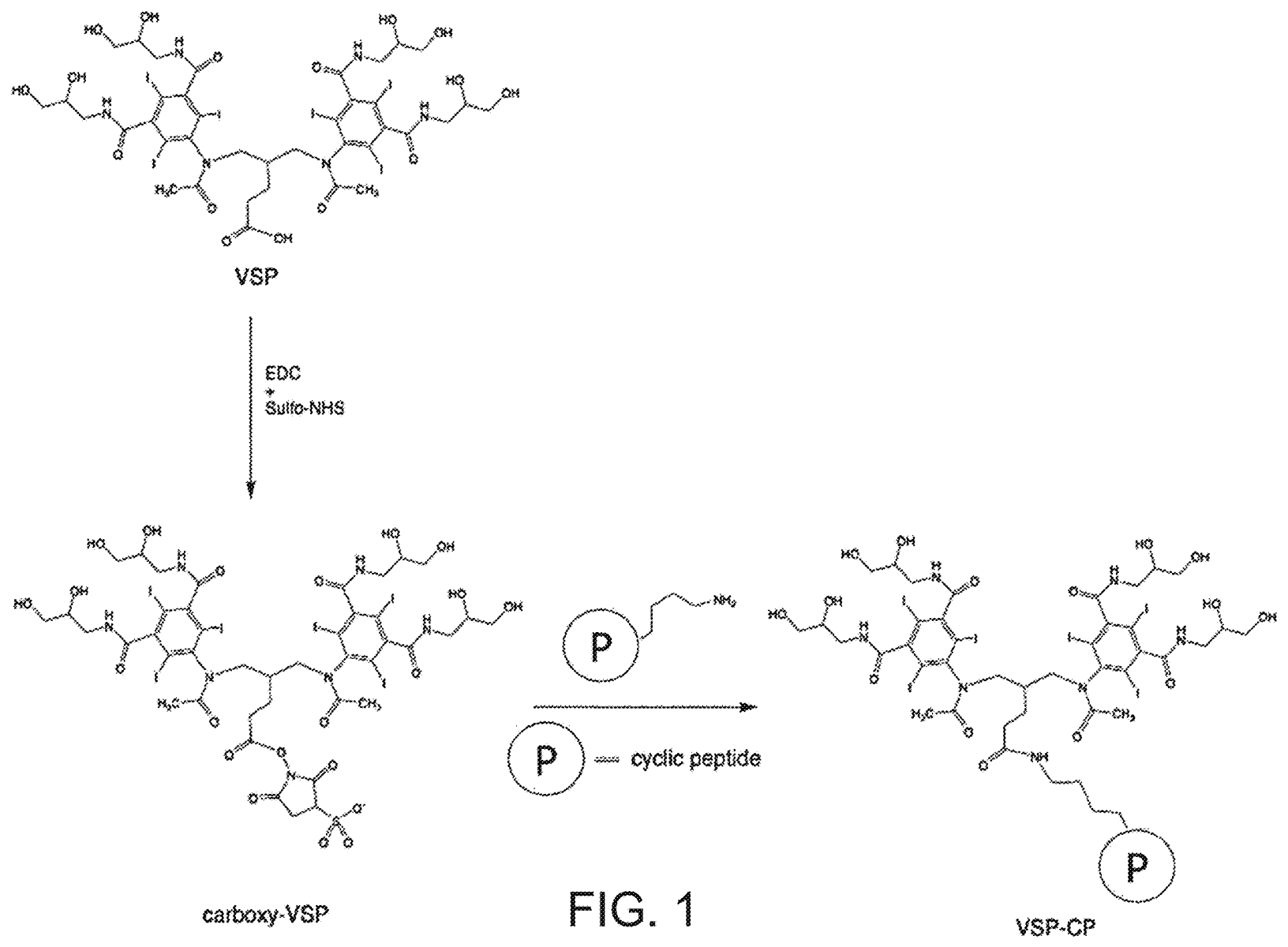

FIG. 1 provides a scheme showing the preparation of a cell penetrating peptide-VSP molecular probe carrier.

Example 2: Preparation of Cell Penetrating Peptide-VSP-TTR Targeting siRNA Molecular Probe An siRNA (customized and synthesized by GenePharma Inc.) targeting liver fibrosis-specific marker gene TTR was used, having the following sequences

```
Sense strand:
                              (SEQ ID NO: 2)
5'-mCAGmUGmUmUmCmUmUGmCmUmCmUAmUAAdTdT-3'

Antisense strand:
                              (SEQ ID NO: 3)
5'-UmUAmUAGAGmCAAGAAmCACUGdTdT-3'
``` where m represents 2' hydroxymethylation of the corresponding base.

The molecular probe was prepared by using the following process:

A). To DEPC water the siRNA was added to the final concentration of 5 µM/mL, for the subsequent use;

B). The molecular probe carrier VSP-CP and the siRNA were mixed at a molar ratio of 20:1, and incubated at room temperature for 15-20 minutes;

C). The siRNA was attached to the molecular probe carrier VSP-CP via a non-covalent interaction to obtain the subject molecular probe.

The so obtained molecular probe can be immediately used for in vitro cell detection or aerosol inhalation detection.

Example 3: Detection of Target Nucleic Acid Using the Cell Penetrating Peptide-VSP-TTR Targeting siRNA Molecular Probe A). Rat BRL3A cells (purchased from ATCC) were seeded in six-well plates at a cell density of $1.2 \times 10^5$ cells/well. 1.5 mL of serum-containing MEM medium was added and the cells were incubated at 37° C. under 5% $CO_2$ for 24 hrs to achieve cell confluence of 40% to 70%.

B). Preparation of molecular probes for transfection:

a. Solution A was the siRNA diluted with serum-free medium, with a final amount of 600 µL and a concentration of 0.4 nm/µL;

b. Solution B was the VSP-CP diluted with serum-free medium, with a final amount of 600 µL and a concentration of 8 nm/µL;

c. Solutions A and B were mixed, gently shaken, and placed at room temperature for 15-20 minutes to form VSP-CP-siRNA molecular probes.

C). Pretreatment for transfection: the cells were washed twice with serum-free medium and the serum-free medium was added 1.3 mL/well to the cells.

D). To the six-well plates, the VSP-CP-siRNA molecular probe was added 200 µL/well, gently shaken, and incubated at 37° C. under 5% $CO_2$ for 24 hrs.

E). At 80 min, 4 hrs, 8 hrs, 12 hrs, 24 hrs, 48 hrs, and 72 hrs after incubation, the cells were washed with PBS for 2 to 3 times, and then detected by CT.

Example 4: Verification of the Effect of TTR Targeting siRNA Targeting TTR mRNA In this example, the effect of TTR targeting siRNA targeting TTR mRNA was verified experimentally.

The results are shown in FIG. 2. Panels 2a, 2b and 2c show the results of fluorescence imaging of rat hepatocytes BRL3A 12 hours after transfection in vitro. Panel 2a shows the result of transfection with TTR-targeting siRNA. Panel 2b shows the result of transfection with NC-siRNA as negative control. Panel 2c shows the result of untransfected cells as blank control. FIG. 2d shows the fluorescence density curves of the group transfected with TTR-targeting siRNA, the group transfected with NC-siRNA as negative control and the untransfected group as blank control at different time points.

According to the results, the intensity of fluorescence shown in Panel 2a is significantly higher than that in Panels 2b and 2c, indicating that the TTR-targeting siRNA successfully entered the cells and specifically bound to the TTR target site. It can be seen from FIG. 2d that BRL3A cells began to show fluorescence gradually after 80 minutes upon transfection, and then the fluorescence gradually accumulated in the cells. The fluorescence density in the cells increased sharply 8 hours upon transfection and reached a peak at 12 hours. It began to decline and gradually stabilized after 24 hours. The best detection time was estimated to be about 12 hours upon the incubation of the probe.

The targeting effect of TTR targeting siRNA was further analyzed by Western blot. 40 nM of TTR-targeting siRNA or NC-siRNA was transfected into BRL3A cells using N-TER as a vector. After 48 hours, the cellular protein was extracted and Western blot was performed to detect the expression of TTR protein in the cells. Untreated BRL3A cells served as a blank control, and β-actin as an internal control. The results are shown in FIG. 3.

Figure 3:
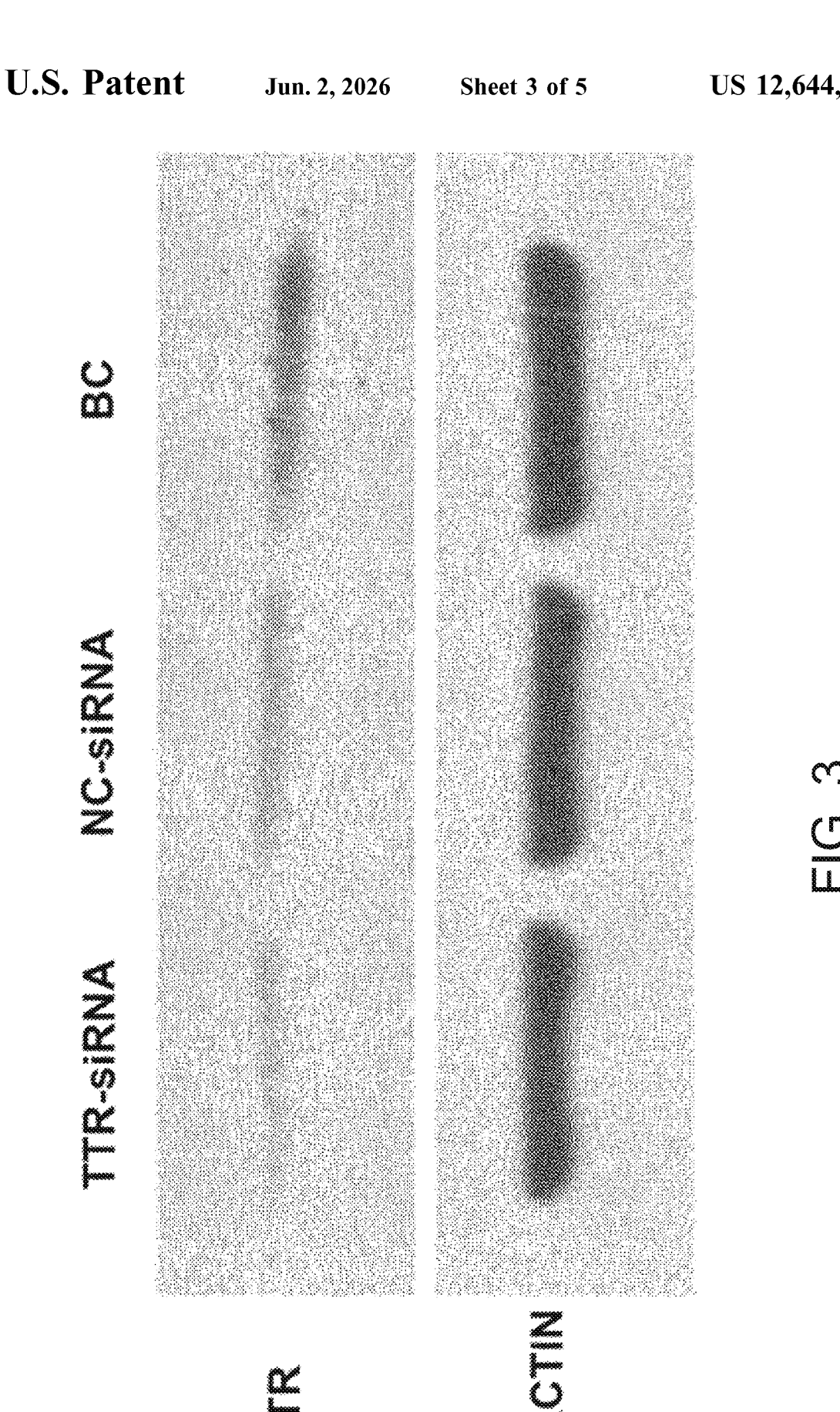
FIG. 3 shows the effect of TTR-targeting siRNA targeting TTR mRNA, analyzed by Western blot.

The results in FIG. 3 show that TTR-targeting siRNA can target and interact with TTR mRNA, thereby inhibiting the expression of TTR protein.

Example 5: Verification of Abnormal Expression of TTR in Liver Fibrosis Model Rats In this example, the abnormal tissue state and abnormal expression of TTR protein under liver fibrosis were verified relative to the normal liver.

Experimental Procedures:

Rats in the healthy group and liver fibrosis model group were sacrificed immediately after the imaging scan was completed, and liver specimens were obtained. After the liver specimen was fixed in 10% formaldehyde for 14 days, a 5 μm paraffin section of the tissue was obtained. The liver specimens of rats in the healthy group and liver fibrosis model group were all treated with HE staining, Masson staining, and pathological staining for TTR molecule for comparison.

HE staining was carried out following the procedures:

1. The paraffin sections were placed in the oven at 60° C. overnight.

2. The sections were taken out of the oven and put in xylene immediately. Sections were treated sequentially with two changes of xylene, 20 minutes each, two changes of 100% ethanol, 5 minutes each, and two changes of 95% ethanol, 5 minutes each, and then dewaxed and placed into water.

3. The sections were washed with TPBS (PBS containing 0.05% Tween-20) for 3 times, 2 minutes each, and put into distilled water.

4. The sections were stained with hematoxylin for 3-5 minutes.

5. Hydrochloric acid ethanol differentiation.

6. Treatment with ammonium hydroxide for 20 seconds (with the color returning to blue).

7. Eosin staining for 2 to 3 minutes.

8. After being spun to dry and dehydrated, the sections were treated sequentially with two changes of 95% ethanol, 5 minutes each, two changes of 100% ethanol, 5 minutes each, and two changes of xylene, 20 minutes each, and then mounted in neutral resin.

Masson staining was carried out following the procedures:

1. The paraffin sections were placed in the oven at 60° C. overnight.

2. The sections were taken out of the oven and put in xylene immediately. Sections were treated sequentially with two changes of xylene, 20 minutes each, two changes of 100% ethanol, 5 minutes each, and two changes of 95% ethanol, 5 minutes each, and then dewaxed and placed into water.

3. Oxidizing with 1% potassium permanganate for 5 minutes.

4. Rinsing with distilled water and bleaching with oxalic acid for 1 minute.

5. Rinsing with distilled water and staining with celestine blue for 5 minutes.

6. Without washing, staining directly with Regaud hematoxylin for 3 to 5 minutes for core staining.

7. Washing thoroughly in distilled water.

8. Treating with ponceau red/acid fuchsin solution for 5 to 10 minutes.

9. Washing with 2% aqueous glacial acetic acid solution for 1 minute.

10. Differentiation with 1% phosphomolybdic acid aqueous solution for 3 to 5 minutes.

11. Without washing, staining directly with aniline blue for 5 minutes.

12. Washing with 0.2% aqueous glacial acetic acid solution for 1 minute.

13. After being spun to dry and dehydrated, the sections were treated sequentially with two changes of 95% ethanol, 5 minutes each, two changes of 100% ethanol, 5 minutes each, and two changes of xylene, 20 minutes each, and then mounted in neutral resin.

Pathological staining for TTR molecule was carried out following the procedures:

1. The paraffin sections were placed in the oven at 60° C. overnight.

2. The sections were taken out of the oven and put in xylene immediately. Sections were treated sequentially with two changes of xylene, 20 minutes each, two changes of 100% ethanol, 5 minutes each, and two changes of 95% ethanol, 5 minutes each, and then dewaxed and placed into water.

3. The sections were washed with TPBS (PBS containing 0.05% Tween-20) for 3 times, 2 minutes each, and put into distilled water.

4. The sections were placed in citrate buffer (pH 6.0) and treated under medium and high heat in a microwave oven for 4 to 5 minutes (to boiling), at a temperature of above 95° C., maintained under low and medium heat for 15 minutes, and cooled naturally at room temperature.

5. The sections were soaked in distilled water for 3 minutes and washed with TPBS for 3 times, 2 minutes each.

6. Horseradish enzyme blocker (3% $H_2O_2$) was added dropwise and incubated for 15 minutes in a wet box at room temperature to eliminate endogenous HRP activity.

7. Washing with TPBS for 3 times, 2 minutes each.

8. Normal goat serum working solution (10% normal goat serum stock solution, diluted with PBS) was added dropwise, incubated at room temperature in a wet box for 30 minutes. The serum was drawn, without washing.

9. Anti-TTR (dilution of sheep serum working solution) was added dropwise (at 1:200 ratio). 4° C., wet box, stayed overnight.

10. The next day, the sections were allowed to reach room temperature and washed 3 times with PBS, 2 minutes each.

11. Reagent 1 from PV-9001 Kit (Zsbio) was added dropwise and the sections were incubated in a wet box for 20 minutes.

12. Washing with TPBS for 3 times, 2 minutes each.

13. Reagent 2 from PV-9001 Kit (Zsbio) was added dropwise, and the sections were incubated in a wet box for 30 minutes.

14. Washing with TPBS for 3 times, 2 minutes each.

15. DAB working solution was prepared immediately before use.

16. The above prepared working solution was added on each section in an amount of 30-40 μL or an amount enough for covering the specimen and the color development was observed under the microscope.

17. Rinsing with distilled water to stop the reaction.

18. Counterstaining with hematoxylin for 2 minutes and washing with distilled water for 5 minutes.

19. Soaking in PBS for 3 minutes (returning to blue) and washing with tap water.

20. After being spun to dry and dehydrated, the sections were treated sequentially with two changes of 95% ethanol, 5 minutes each, two changes of 100% ethanol, 5 minutes each, and two changes of xylene, 20 minutes each, and then mounted in neutral resin.

Figure 4:
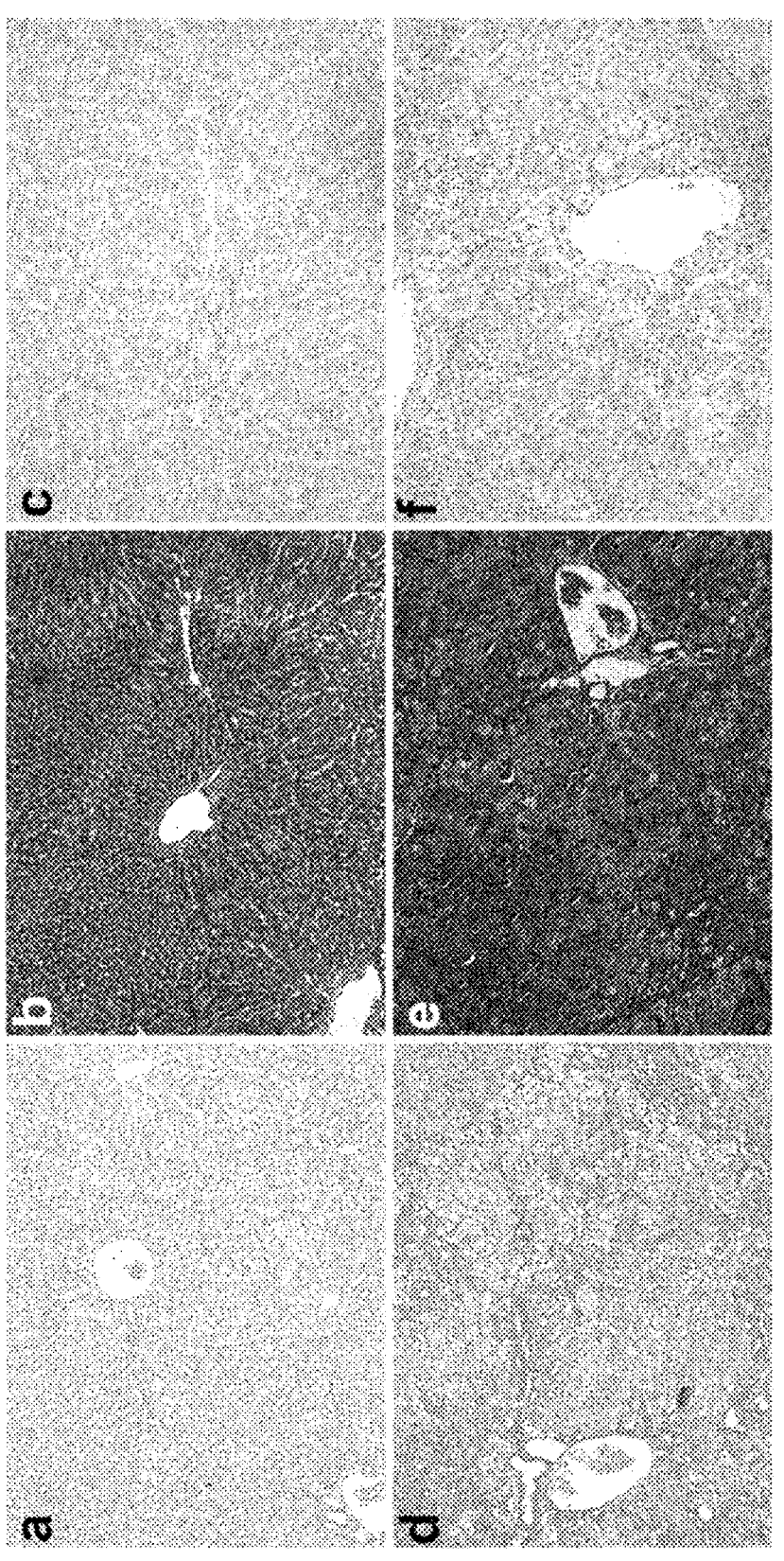
FIG. 4 shows the abnormal tissue state and abnormal expression of TTR protein in the case of liver fibrosis disorders relative to normal liver. Panels 4a to 4c show the results of HE, Masson and TTR protein immunohistochemical staining in healthy rats. Panels 4d to 4f show the results of HE, Masson and TTR protein immunohistochemical staining in liver fibrosis model rats.

The results are shown in FIG. 4. Panels 4a-4c show the results of HE, Masson and TTR protein immunohistochemical staining in healthy rats; Panels 4d-4f show the results of HE, Masson and TTR protein immunohistochemical staining in liver fibrosis model rats.

It is shown that the liver TTR protein expression of liver fibrosis model rats was significantly higher than that of normal healthy rats. Accordingly, liver TTR protein can be used as a marker for detection of liver fibrosis.

Example 6: In Vivo Detection of Healthy and Liver Fibrosis Model Rats Using 18F-TTR Targeted siRNA Probes In this example, 18F-TTR targeted siRNA probes were used in in vivo detection of healthy and liver fibrosis model rats.

Experimental Procedures:

The rats in the healthy group and the liver fibrosis model group were subjected to PET/CT imaging in the fourth week after treatment with thioamide solution. Before imaging, rats were water-free and fasted for 6 hours. The rats were intraperitoneally injected with 10% chlorohydrate in an amount of 0.3 mL/100 g for anesthesia before imaging. Rats in liver fibrosis model and control group were injected with 0.5 mCi 18F-TTR targeting siRNA probe through the tail vein. The rats were dynamically scanned. The PET scan layer thickness was 3.75 mm. The CT scan parameters were 80 kV, 50 mA. The layer thickness: 3.75 mm. After the CT scan, the PET dynamic scan was continued for 60 minutes, and the regular scan was performed at the 80th minute. The collected images were pre-treated by SharpIR, VUE Point HD image reconstruction technology and OSEM iterative reconstruction method, and treated using GE AW4.5 and Xeleris 3.0 workstations. 3D PET and CT fusion images of the cross-section, sagittal plane, and coronal plane of rat liver and the radioactivity as a function of time were shown in FIG. 5.

Figure 5:
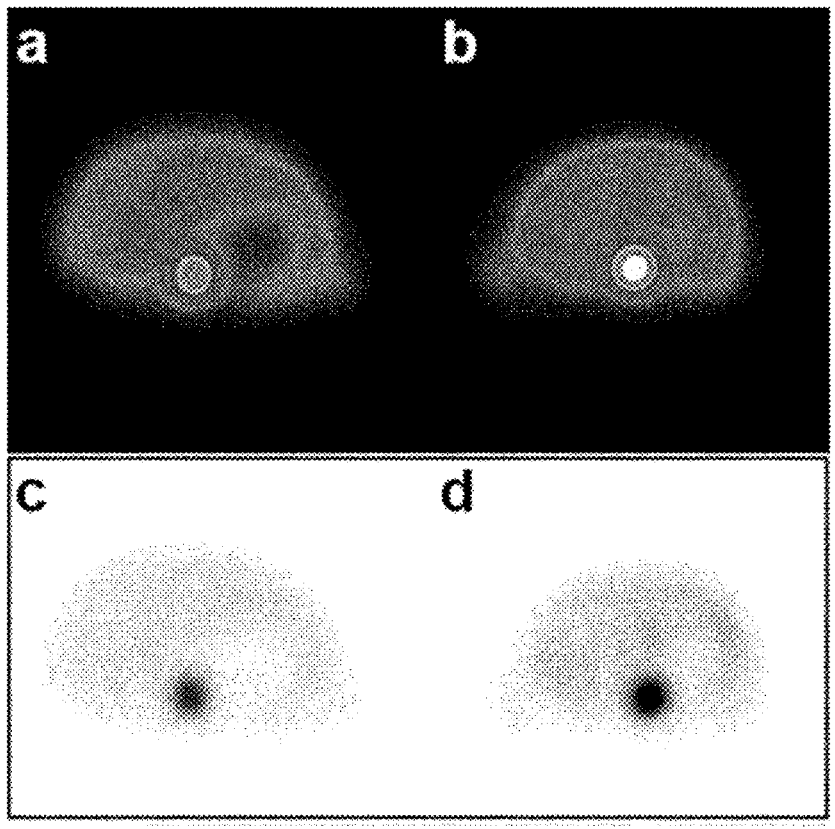
FIG. 5 shows the uptake of 18F-TTR-targeting siRNA molecular probes by the livers of healthy rats and liver fibrosis model rats. Panels 5a and 5c are the pseudo-color and gray-scale PET imaging of the molecular probe accumulated in the liver fibrosis model group 60 minutes after injection of the probe. Panels 5b and 5d are the pseudo-color and gray-scale PET imaging of the molecular probe accumulated in the healthy rats 60 minutes after injection of the probe. Panel 5e shows the radioactivity of the molecular probe in the liver fibrosis model group and the liver of healthy rats as a function of time.
Figure 5:
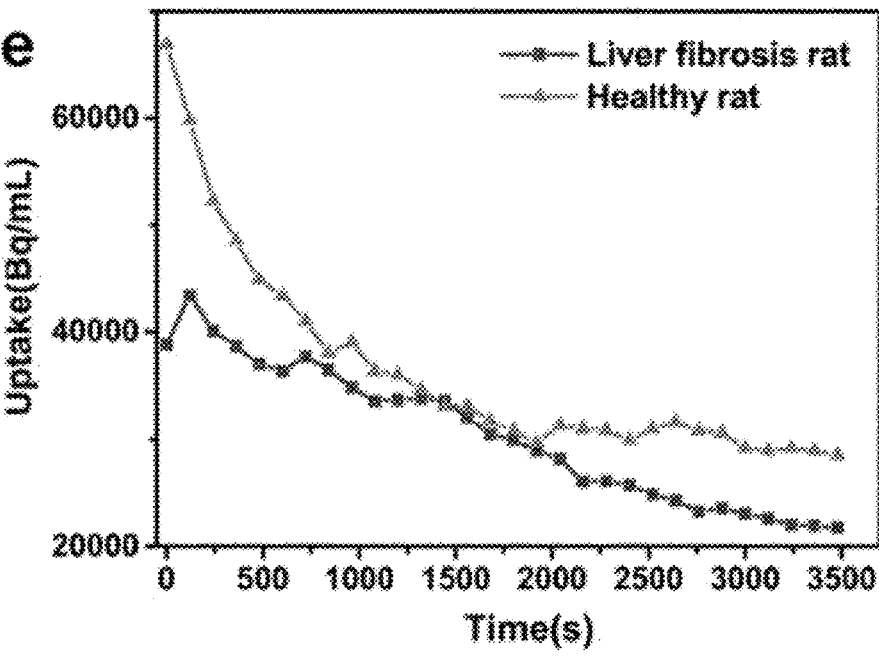

FIG. 5 shows the uptake of 18F-TTR-targeting siRNA molecular probes by the livers of healthy rats and liver fibrosis model rats. Panels 5a and 5c are the pseudo-color and gray-scale PET imaging of the molecular probe accumulated in the liver fibrosis model group 60 minutes after injection of the probe. Panels 5b and 5d are the pseudo-color and gray-scale PET imaging of the molecular probe accumulated in the healthy rats 60 minutes after injection of the probe. Panel 5e shows the radioactivity of the molecular probe in the liver fibrosis model group and the liver of healthy rats as a function of time.

It is shown that liver radioactivity of liver fibrosis rats and healthy rats decreased with time. The radioactivity difference between the two groups began to appear at the 24th minute after injection of the probe, and the tracking rate of the liver of healthy rats became significant at the end of the scan (80 minutes after injection).

It is demonstrated by the results of FIGS. 4 and 5 that the molecular probes targeting TTR mRNA can be useful for non-invasive detection of liver fibrosis.

Example 7: Preparation of Alternative Cell Penetrating Peptide-VSP-siRNA Molecular Probes In this example, CP-VSP-siRNA molecular probes carrying other disease-specific siRNA molecules were prepared for nucleic acid detection of the corresponding disorders or diseases.

(1) Preparation of Cell Penetrating Peptide-SARS-CoV-2 Targeting siRNA Molecular Probe An siRNA (customized and synthesized by GenePharma Inc.) targeting the genome of new coronavirus was used, having the following sequences:

```
Sense strand:
                                    (SEQ ID NO: 4)
5'-GCGAAAUACCAGUGGCUUAdTdT-3';
or
                                    (SEQ ID NO: 5)
5'-GCUACUAAUGGACCACUUAdTdT-3'.
```

The molecular probe was prepared following the procedures:

A). To DEPC water the siRNA was added to the final concentration of 5 μM/mL, for the subsequent use;

B). The molecular probe carrier VSP-CP (prepared according to Example 1) and the siRNA were mixed at a molar ratio of 20:1, and incubated at room temperature for 15-20 minutes;

C). The siRNA was attached to the molecular probe carrier VSP-CP via a non-covalent interaction to obtain the subject molecular probe.

The so obtained molecular probe can be immediately used for in vitro cell detection or aerosol inhalation detection.

(2) Preparation of Cell Penetrating Peptide-IAV Targeting siRNA Molecular Probe

An siRNA (customized and synthesized by GenePharma Inc.) targeting the genome of influenza A virus was used, having the following sequences:

```
Sense strand:
                                    (SEQ ID NO: 6)
5'-CAAGCAGUGUGUACAUUGAdTdT-3';
or (SEQ ID NO: 7)
5'-GGAGACGUGGUGUUGGUAAdTdT-3'.
```

The molecular probe was prepared following the procedures:

A). To DEPC water the siRNA was added to the final concentration of 5 µM/mL, for the subsequent use;

B). The molecular probe carrier VSP-CP (prepared according to Example 1) and the siRNA were mixed at a molar ratio of 20:1, and incubated at room temperature for 15-20 minutes;

C). The siRNA was attached to the molecular probe carrier VSP-CP via a non-covalent interaction to obtain the subject molecular probe.

The so obtained molecular probe can be immediately used for in vitro cell detection or aerosol inhalation detection.

Example 8: In Vitro Nucleic Acid Detection of the Molecular Probe According to Example 7

A). Cells (adherent) obtained from the subject to be detected were seeded in six-well plates at a cell density of $1.2 \times 10^5$ cells/well. 1.5 mL of serum-containing MEM medium was added and the cells were incubated at 37° C. under 5% $CO_2$ for 24 hrs to achieve cell confluence of 40% to 70%.

B). Preparation of molecular probes immediately before transfection:

a. Solution A was the siRNA (siRNA as described in Example 7) diluted with serum-free medium, with a final amount of 600 µL at a concentration of 0.4 nm/µL;

b. Solution B was the VSP-CP diluted with serum-free medium, with a final amount of 600 µL at a concentration of 8 nm/µL;

c. Solutions A and B were mixed, gently shaken, and placed at room temperature for 15-20 minutes to form VSP-CP-siRNA molecular probes.

C). Pre-treatment for transfection: the cells were washed twice with serum-free medium and fresh serum-free medium was added 1.3 mL/well to the cells.

D). To the six-well plates, the VSP-CP-siRNA molecular probe was added 200 µL/well, gently shaken, and incubated at 37° C. under 5% $CO_2$ for 12 hrs.

E). After the incubation, the cell culture medium was half-volume exchanged with the cell culture medium containing 20% fetal bovine serum, and the cells were placed at 37° C. under 5% $CO_2$ for a duration of time of from 80 minutes to 72 hours. Then the cells were washed with the medium and observed using CT for detection of the presence and/or level of the targets.

It should be understood that after reading the above teaching content of the present disclosure, those skilled in the art can make various changes or modifications to the technical solutions disclosed herein, and these equivalent forms also fall within the scope defined by the appended claims of the present disclosure.

---

The invention claimed is:

1. A molecular probe for detection of a nucleic acid, comprising,
   (1) a molecular probe carrier comprising
   a cell penetrating peptide wherein the cell penetrating peptide comprises an amino acid sequence having 100% sequence identity with the amino acid sequence set forth in SEQ ID NO: 1;
   and a detectable label coupled to the cell penetrating peptide wherein the detectable label is coupled to a lysine residue comprised in the cell penetrating peptide, and
   (2) a targeting oligonucleotide, wherein the targeting oligonucleotide is attached to the molecular probe carrier.

2. The molecular probe according to claim 1, wherein the detectable label is a contrast agent.

3. The molecular probe according to claim 2, wherein the contrast agent is iodixanol.

4. A method for preparing a molecular probe, comprising,
   coupling a detectable label to a cell penetrating peptide to obtain a molecular probe carrier, wherein the cell penetrating peptide comprises an amino acid sequence having 100% sequence identity with the amino acid sequence set forth in SEQ ID NO: 1 and the detectable label is coupled to a lysine residue comprised in the cell penetrating peptide;

incubating the molecular probe carrier with a targeting oligonucleotide for a duration of time sufficient to allow attachment between the molecular probe carrier and the targeting oligonucleotide, to obtain the molecular probe.

5. The method according to claim 4, further comprising modifying the detectable label prior to incubating, wherein the resulting modified detectable label comprises a moiety for attachment to the cell penetrating peptide.

6. A method for detection of a nucleic acid, comprising,
   applying a molecular probe according to claim 1 to a subject or a sample from the subject; and
   determining a presence and/or a level of a target nucleic acid by detecting the detectable label in the subject or the sample from the subject.

7. The method according to claim 6, further comprising before applying the molecular probe, preparing the molecular probe from the molecular probe carrier and the targeting oligonucleotide by a one-step process.

8. A kit for detection of a nucleic acid, comprising,
   a container comprising the molecular probe carrier as defined in claim 1 and a container comprising the targeting oligonucleotide as defined in claim 1.

* * * * *